United States Patent
Datta et al.

(10) Patent No.: US 6,821,379 B2
(45) Date of Patent: Nov. 23, 2004

(54) PORTABLE APPARATUS AND METHOD FOR TREATING A WORKPIECE

(75) Inventors: Saswati Datta, Cincinnati, OH (US); John Andrew McDaniel, Middletown, OH (US); Seyed Farhad Miralai, Fairfield, OH (US); Vesselin Nikolov Shanov, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 323 days.

(21) Appl. No.: 10/027,646

(22) Filed: Dec. 21, 2001

(65) Prior Publication Data

US 2003/0155332 A1 Aug. 21, 2003

(51) Int. Cl.$^7$ ............................ H05H 1/00; C23C 16/00
(52) U.S. Cl. ................................ 156/345.43; 118/723 E
(58) Field of Search ........................ 156/345.43, 345.35, 156/345.44, 345.45, 345.47; 118/715, 723 R, 723 E, 723 ER, 254

(56) References Cited

U.S. PATENT DOCUMENTS

| | | |
|---|---|---|
| 4,652,723 A | 3/1987 | Salinier et al. |
| 5,084,126 A | 1/1992 | McKee |
| 5,236,512 A | 8/1993 | Rogers et al. |

(List continued on next page.)

FOREIGN PATENT DOCUMENTS

| | | |
|---|---|---|
| DE | 19605226 A1 | 8/1997 |
| EP | 1 162 646 A2 | 12/2001 |
| JP | 05251198 | 9/1993 |
| JP | 2001-159074 | 6/2001 |
| WO | WO 00/79843 A1 | 12/2000 |
| WO | WO 01/44790 A1 | 6/2001 |
| WO | WO 02/28548 A2 | 4/2002 |
| WO | WO 02/065820 A1 | 8/2002 |
| WO | WO 02/099836 A1 | 12/2002 |

OTHER PUBLICATIONS

Takaki, et al., "Multipoint Barrier Discharge Process for Removal of NOx from Diesel Engine Exhaust", IEEE Transactions on Plasma Science, vol. 29, No. 3, Jun. 2001.

Bayer, et al., "Overall kinetics of $SiO_x$ remote–PECVD using different organosilicon monomers", Surface and Coatings Technolog 116–119 (1999), pp. 874–878.

Karches et al., "A circulating fluidized bed for plasma–enhanced chemical vapor deposition on powders at low temperatures", Surface and Coatings Technology 116–119 (1999) pp. 879–885.

ASTEX®, "Downstream Sources for Etch and Deposition," Feb. 1, 1991, Applied Science Technology, Inc., Woburn, Mass.

ASTEX©, "Providing Innovation in Plasma, Power and Reactive Gases," Jan.–Feb., 2001, Applied Science Technology, Inc., Woburn, Mass.

AX7200, Atmospheric Plasma Torch instructions, received May, 2001.

Primary Examiner—Parviz Hassanzadeh
(74) Attorney, Agent, or Firm—Larry L. Huston; Leonard W. Lewis; Steven W. Miller (57) ABSTRACT

A plasma generating apparatus and method for treating a surface of a workpiece. This apparatus comprises a power supply 100, at least one powerable electrode connected to the power supply 100, at least one groundable electrode connected to ground, a dielectric separating the at least one powerable electrode and the at least one groundable electrode, a chamber at least partially housing both the powerable electrode and the groundable electrode and a first inlet for admitting a first gas into the chamber such that the first gas can flow between the at least one powerable electrode and the at least one groundable electrode. The at least one powerable electrode and the at least one groundable electrode are disposed in an array. These electrodes are arranged to be on a common side of a workpiece, to provide a portable apparatus.

13 Claims, 4 Drawing Sheets

U.S. PATENT DOCUMENTS

| | | | |
|---|---|---|---|
| 5,387,842 A | | 2/1995 | Roth et al. |
| 5,403,453 A | | 4/1995 | Roth et al. |
| 5,549,780 A | * | 8/1996 | Koinuma et al. ...... 156/345.39 |
| 5,671,045 A | | 9/1997 | Woskov et al. |
| 5,961,772 A | * | 10/1999 | Selwyn .................. 156/345.39 |
| 6,005,349 A | | 12/1999 | Kunhardt et al. |
| 6,081,329 A | | 6/2000 | Cohn et al. |
| 6,194,036 B1 | | 2/2001 | Babayan et al. |
| 6,244,211 B1 | * | 6/2001 | Nishikawa et al. ... 118/723 AN |
| 6,262,523 B1 | | 7/2001 | Selwyn et al. |
| 6,406,590 B1 | * | 6/2002 | Ebata et al. ........... 156/345.43 |
| 6,632,323 B2 | * | 10/2003 | Kim et al. ............. 156/345.43 |
| 2002/0195950 A1 | | 12/2002 | Michael et al. |
| 2003/0052096 A1 | * | 3/2003 | Crowe et al. .......... 219/121.43 |

* cited by examiner

PORTABLE APPARATUS AND METHOD FOR TREATING A WORKPIECE

FIELD OF THE INVENTION

The present invention relates to an apparatus and method for treating a surface of a workpiece using plasma discharge wherein the apparatus is movable about the workpiece during treatment and operable at atmospheric pressure.

BACKGROUND OF THE INVENTION

Plasmas, such as are described herein, are partially ionized gases and consist of ions, electrons and neutral species. Plasma is state of matter produced by the action of DC or AC fields having RF or MW frequencies. Plasmas can be useful for treating the surface of a workpiece.

Low power density, low intensity plasmas, such as dark discharges and corona discharges, have been used at low pressure and at one atmosphere for the surface treatment of various materials. However, due to the relatively low energy density, these discharges alter surface properties of materials relatively slowly, if at all. Also, corona discharges are non-uniform and filamentary in nature. This may lead to localized arcs known as "hot spots" and non-uniform surface modification. Generally, the use of corona discharges for treating the surface of a workpiece is unsatisfactory.

Glow discharge plasmas are produced by free electrons energized by an imposed DC, photon beam or RF electric field. This field causes electrons to collide with the neutral species. These collisions form a variety of active species which may include, excited atoms and molecules, metastables, free radicals, molecular fragments, electrons and ions, as well as ultraviolet and visible photons.

Glow discharge plasma has been successfully used in low pressure environments (e.g., below 10 Torr). In many applications, glow discharge provides active species which produce important effects, but generates temperatures high enough or requires treatment times long enough to damage the surface of the workpiece being treated.

Glow discharge plasmas are typically generated in low pressure environments. This constraint usually necessitates the treatment of workpieces within a vacuum system. Alternatively, glow discharge plasmas may be generated, for example, using the one atmosphere uniform glow discharge plasma reactors described in U.S. Pat. Nos. 5,387,842 and 5,403,453, both issued to Roth, et al, on Feb. 7, 1995, and Apr. 4, 1995, respectively.

Most of this work has been performed in a laboratory environment and has been limited to very small scale operations. The workpiece is limited to the size of the chamber. To treat a workpiece of any size, such as a garment, the chamber must be large enough to allow the garment to be disposed within the chamber. Generally, this will require the vacuum system to be big, bulky and expensive. Furthermore, such a chamber is typically stationary and thus requires the workpiece to be moved and placed within the chamber. This type of system cannot be used with a stationary workpiece.

Plasma treatments, such as plasma etching, deposition, cleaning or sanitization of a workpiece, can change the surface properties of the workpiece. Plasma etching can remove small amounts of material from the surface, thereby also removing surface contaminants and/or exposing a fresh surface for subsequent processing. Plasma etching can be used for applications such as sterilizing, cleaning, etc. of surfaces of a workpiece. Plasma-cleaned surfaces may provide for adhesion of electroplated layers or paint and stronger adhesive bonding of substances to the surface. Plasma etching may be useful for skin cleaning, hair cleaning, window cleaning, etc. Plasma etched surfaces may have modified moisture uptake properties, useful in applications such as household painting, nail polishes, hair coloring, skin moisturizing, etc.

Plasma deposition can deposit a thin layer or coating on the surface of a workpiece, providing improved surface properties such as hydrophobicity, hydrophilicity, oleophobicity or oleophilicity. Such surface properties may provide stain resistant fabrics, or superabsorbent material on the substrate. Plasma deposited coatings can be used on a variety of workpieces such as shoes, carpets, upholstery, decks, etc.

U.S. Pat. No. 5,961,772 iss. Oct. 5, 1999 to Selwyn and U.S. Pat. No. 6,262,523 B1 iss. Jul. 17, 2001 to Selwyn et al., disclose an atmospheric-pressure plasma jets using cylindrical and planar electrodes, respectively. DE 19,605,226, discloses a device to generate plasma using a plurality of parallel electrodes protruding from a surface. U.S. Pat. No. 5,236,512, issued Aug. 17, 1993 to Rogers, et al. discloses a device for cleaning a surface by introducing a highly reactive gas mixture to the surface. These teach devices having a single electrode pair/gas flow channel which makes it difficult to effectively treat a large surface area.

WO 01/44790 published Jun. 21, 2001 in the names of Korfiatis et al teaches a plasma reactor having at least one segmented electrode. In the reactor, a fluid passes through caplillaries and impinges on the surface of a dielectric. After impinging on the dielectric, the fluid changes direction and exits from the reactor. This arrangement provides the disadvantages that plugging of the capilaaries may occur and significant deposition on the wall of the dielectric may occur, and cause undesirable deactiviation of any active species in the fluid. U.S. Pat. No. 6,005,349 issued Dec. 21, 1999 to Kunhardt et al. teaches a glow pasma apparatus having a perforated dielectric with micro-channel apertures therethrough and separating two electrodes.

U.S. Pat. No. 5,671,045 issued to Woskov et al. on Sep. 23, 1997, and U.S. Pat. No. 6,081,329 issued to Cohn et al. on Jun. 27, 2000, disclose atmospheric pressure microwave plasma devices. These devices are used to activate atoms for trace element monitoring and analysis of solid, liquid and gas samples, based on the principles of the atomic emission spectroscopy. The device does not include a plasma enhancer or process chamber for treating a surface of a work-piece. Furthermore, these references fail to teach deposition/polymerization/etching, or other surface modifications.

The present invention provides an atmospheric-pressure, plasma generating apparatus and method to treat a surface of a workpiece. The present invention also provides an atmospheric-pressure, plasma generating apparatus and method to treat a surface of a workpiece, wherein the apparatus is movable about the surface of the workpiece during treatment.

SUMMARY OF THE INVENTION

In one embodiment the invention copmrises an atmospheric-pressure, plasma generating apparatus for treating a surface of a workpiece. The apparatus comprises: at least one powerable electrode connectable to a power supply and powerable by the power supply, at least one groundable electrode connectable to a ground and a dielectric intermediate the powerable electrode and groundable electrode. A first plurality of powerable electrodes and groundable electrodes 50 are disposed in pairs, each pair generating a plasma zone and operatively associated with a second plurality of flow channels, whereby a plasma gas can flow through the flow channels and thereby produce a plasma therein upon interaction with the powerable electrode when it is powered. The plasma is capable of interacting with a working gas to produce an excited species. A third plurality of outlets from the flow channels, allow the excited species to exit the flow channels. The outlets are juxtaposable with a workpiece whereby the excited species may flow through the outlets to impinge on the surface of the workpiece. The flow of the excited species occurs in a primary direction which is straight and unobstructed from the plasma to the surface of the workpiece. In another embodiment the invention comprises a method of treating a surface of a workpice in accordance with the foregoing.

DETAILED DESCRIPTION

Figure 1:
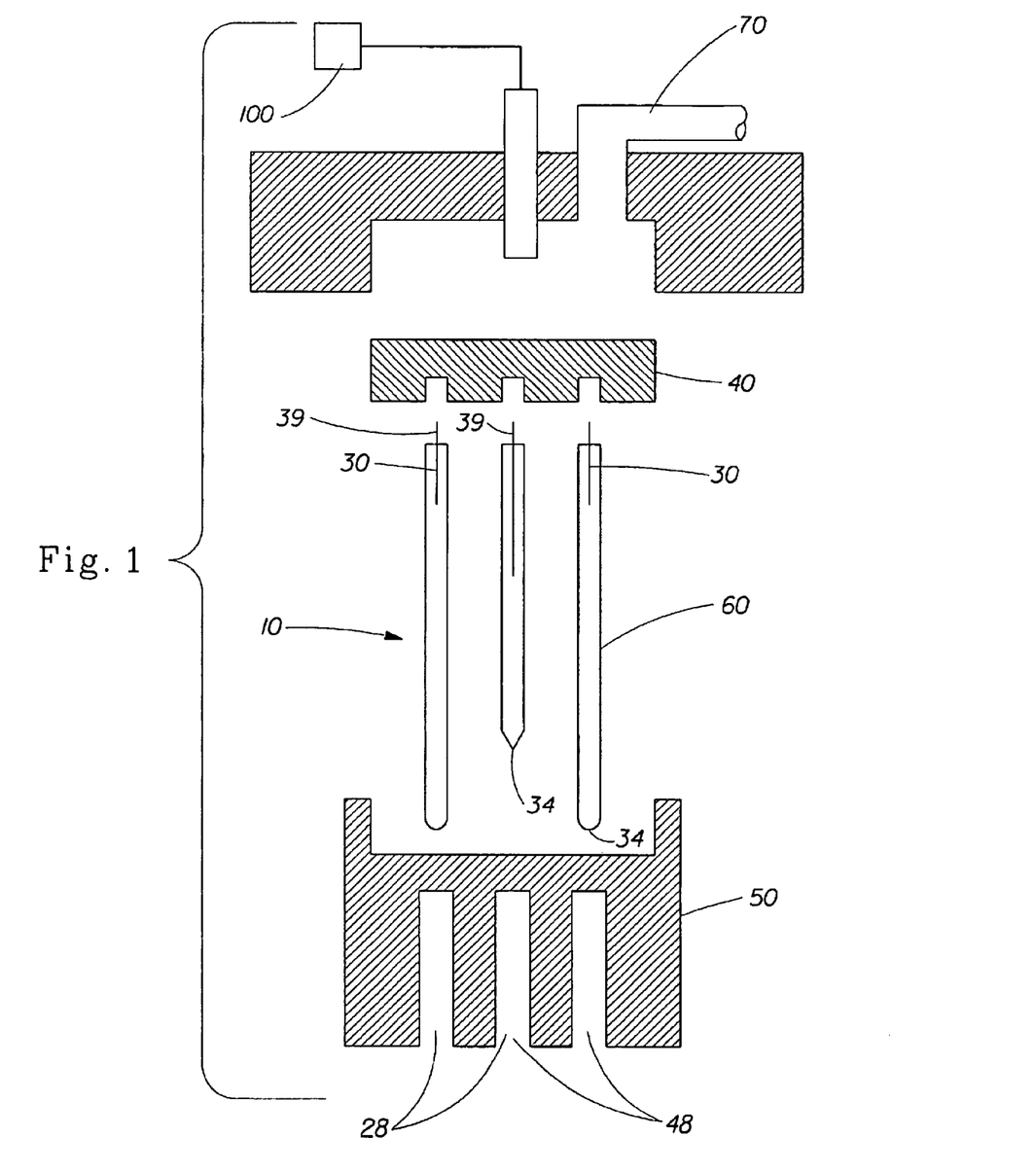
FIG. 1 is an exploded view of an apparatus according to the present invention and having elongate flow channels with electrodes disposed therein.
Figure 2:
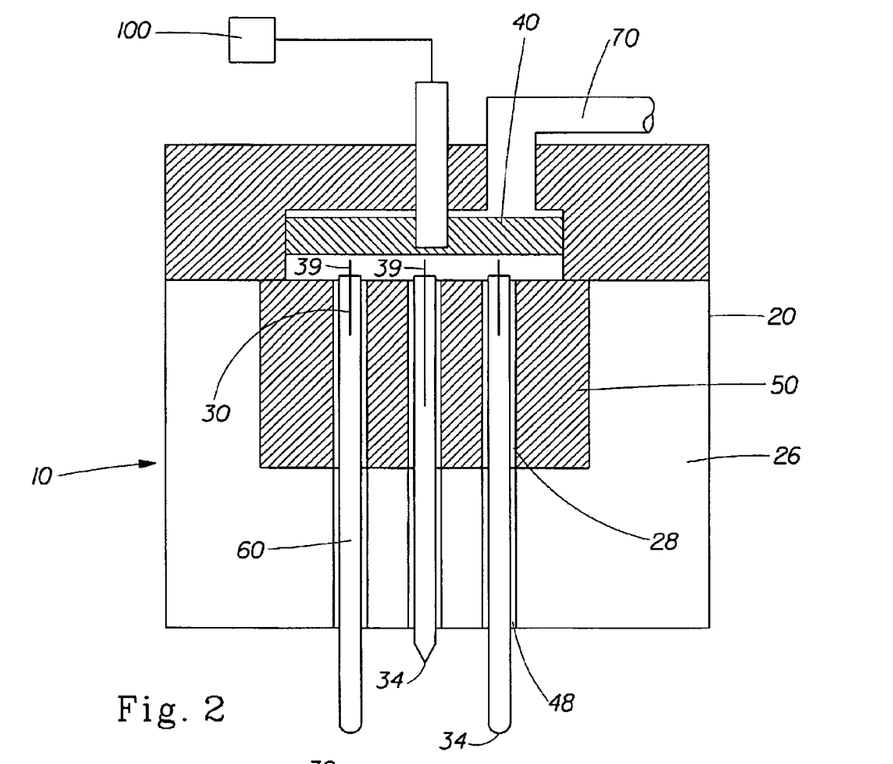
FIG. 2 is a vertical sectional view of the electrode assembly of FIG. 1, showing different lengths of electrodes disposed in the flow channels.
Figure 3:
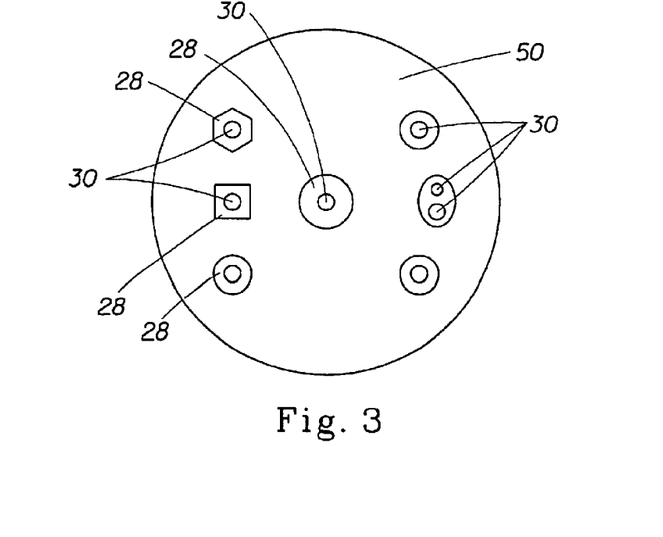
FIG. 3 is a bottom plan view of the electrode assembly shown in FIG. 2.

Referring to FIGS. 1–3, apparatus 10 is an atmospheric pressure plasma-generating apparatus 10 for treating a surface of a workpiece. Apparatus 10 comprises a chamber 20, at least one powerable electrode 30 optionally disposed at least partially in chamber 20, at least one groundable electrode 50 spaced a distance from the powered electrode 30 and optionally at least partially disposed in a chamber 20, a first gas inlet 70 for admitting a first gas into chamber 20 and a dielectric 60 separating powerable electrode 30 from groundable electrode 50.

Apparatus 10 may use a dielectric 60 barrier discharge to generate plasma, and particularly non-equilibrium, medium density and/or low temperature plasma. Apparatus 10 generates plasma at or near atmospheric pressure, wherein the pressure ranges from about 200 Torr to about 2500 Torr, preferably about 760 Torr. This allows the user to treat surface while it is at approximately ambient pressure.

The discharge pattern may be either filamentary or preferably glow-like, depending on the operating parameters and chemistry of the plasma gas. This type of plasma allows any kind of workpiece to be treated without altering its bulk properties. The plasma density in a dielectric 60 barrier discharge apparatus 10 is of the same order of magnitude as obtained with low pressure apparatus 10, however, the density of excited species, including radicals and metastables is much higher in a dielectric 60 barrier discharge apparatus 10.

The surface of the workpiece may be treated in its entirety, or alternatively only selected portions of the surface may be treated. The surface, or selected portions thereof, of the workpiece to be treated is referred to as the "target surface." The workpiece may comprise a variety of planar or three dimensional, intermediate or finished items and raw materials such as but not limited to skin, hair, other human parts, metal, wood, other natural materials, woven or nonwoven substrates, polymers, paper, water, plastic, cloth or other material. The workpiece may be composed of composite materials such as polymer blends, polymer coated metal substrates, substrates with paint coating or materials with dye incorporated into it and may include without limitation furniture, upholstery, garments, carpets, walls, tabletops, countertops, etc.

Apparatus 10 is optionally portable. The term, "portable apparatus 10" as used herein is an apparatus 10 movable to the remote location of a workpiece, such as a home, office or vehicle. The term, "portable" denotes the ability for the apparatus 10 to treat items that are temporarily or permanently immovable, stationary or affixed and which could not ordinarily be treated due to difficulty placing the workpiece inside the apparatus 10. Preferably, the portable apparatus 10 has a weight and size to be conveniently handheld by a user. The apparatus 10 may have a weight less than about 23,000 grams (g), more preferably less than about 11,500 g. Apparatus 10 includes chamber 20 having an interior volume 26 for plasma generation and the flow of gas thereby and interaction therewith. Chamber 20 may also channel excited species towards surface. Chamber 20 can include an enclosure that encompasses a powerable electrode 30, groundable electrode 50, flow channels 28; at least one gas inlet 70 for admitting first gas and an outlet 48 to permit excited species, to be exposed to surface. The apparatus 10 may optionally have a cooling device incorporated therein, as is well known in the art.

A powerable electrode 30 is an electrode which can be charged upon connection to a power supply 100, and thereby become a powered electrode 30. A groundable electrode 50 is an electrode which can be connected to a suitable ground and thereby become a grounded electrode 50. The terms powerable/ed electrode 30 and groundable/ed electrode 50 are considered to be interchangeable, as the context permits, and designate mutually opposite electrodes. The apparatus 10 has at least two such opposite electrodes 30, 50 preferably disposed on a common side of the workpiece being treated.

Powered electrode 30 and grounded electrode 50 may form an array that comprises at least three electrodes 30, 50 having at least two opposite electrodes 30, 50 disposed on a common side of workpiece. This array preferably provides for uniform plasma treatment across surface or a portion thereof, without requiring larger sized electrodes. Larger sized electrodes 30, 50 have the disadvantage of requiring more power to operate, thereby increasing safety concerns. The electrodes 30, 50 may be made from any electrically conductive material including but not limited to aluminum, tin, tungsten, copper, stainless steel, nickel or gold.

Powered electrodes 30 may be disposed in an array comprising a plurality of individual powerable and/or powered electrodes 30. Array, as used herein, can be any arrangement of powered electrodes 30, grounded electrodes 50, or combinations thereof forming a regular or irregular geometric arrangement. The array of electrodes 30, 50 according to the present invention provides a plurality of plasma zones, with a plasma zone formed by each opposite electrode 30, 50 pair. A plasma zone is any region which can act upon a working gas to produce usable excited species. Providing a plurality of plasma zones is more desirable than a single plasma zone, as the electrodes 30, 50 needed to power a single plasma zone large enough to be suitable for use with the present invention would require undue power levels, increasing safety concerns.

A dielectric 60 separates powered electrode 30 from grounded electrode 50. Dielectric 60 may comprise any material having a suitable dielectric 60 constant a relatively smooth surface such that it does not lead to the formation of arcs or hot spots including but not limited to glass, ceramics, plastics, polymides such as KAPTON®, and TEFLON®, oxides such as Barium titanate, aluminum oxide, etc. Dielectric 60 may take any shape or form but should generally conform to and preferably contact the powered electrode 30. Optionally a second dielectric 60 can also cover grounded electrode 50

Grounded electrode 50 is spaced apart from powered electrode 30 a distance (d) about 10 microns to about 20 mm, preferably about 0.2 to about 3 mm, and more preferably about 0.5 to about 1 mm. A distance (d) less than about 10 microns presents manufacturing difficulties due to the tolerance requirements. As distance (d) increases to more than 20 mm, the voltage requirements become too great. Many combinations of powered eletrodes and grounded electrodes 50 are feasible, and the spacing between a powered and grounded electrode 30, 50 pair may vary or be constant within the aforementioned ranges and vary outside such range in a less preferred embodiment. It is to be recognized that plural powered electrodes 30 may share a common grounded electrode, or vice versa and form a like number of electrode 30, 50 pairs.

Gas distribution device promotes the desired typically uniform, distribution of the gasses used in the process to flow channels 28 and ultimately to outlets 48. The distribution of gasses among the flow channels 28 may be equal or unequal, as desired. The gas distribution device may be a header which equalizes the pressure drop of gasses entering flow channels 28. Gas distribution device includes one or more apertures having powered electrodes 30 disposed therein. An arrangement having a powered electrode 30 dedicated to each aperture is illustrated, or a plurality of powered electrodes 30 may be disposed in each aperture. Surrounding each powered electrode 30 is a flow channel 28 to permit gas to flow from interior volume 26 into flow channels 28 located between powered electrode 30 and grounded electrode 50.

The term, "gas source" includes the supply line(s) and connection(s) necessary to supply the gas from a gas storage source or container to the first inlet 70. Gas source can be internal or external to apparatus 10. The working gas and/or plasma gas can comprise a single gas or a combination of gases and vapors. The surface modification of the workpiece is typically dependent upon the working gas. Working gas is preferably a monomer. The working gas may be selected from saturated hydrocarbons, such as methane, ethane, etc., unsaturated hydrocarbons such as ethylene, propylene, etc., hydrocarbons having or not having halogen or other functional groups and fluorocarbons such as Perfluoromethylcyclohexane (PFMCH), tetrafluorethane, perfluorohexene, etc. For example, to sanitize workpieces, a working gas such as argon, argon plus oxygen, argon plus tetrafluorocarbon, halogenated hydrocarbons, etc. may be used. For non-fouling coatings, such as are usable for contact lenses, working gas may comprise poly-ethylene-oxide. For bonding of proteins, working gas may comprise an amine base. To create non-wettable coatings on the surface, working gas typically comprises a fluorocarbon siloxane, or hydrocarbon.

Apparatus 10 and all of its components as set forth above, including the gas source and power supply 100 can be enclosed and incorporated into a single package, creating a portable device that can be hand held. Or, apparatus 10 can have all of the components in a unitary package, except the gas storage tank(s) and/or power supply 100 which may be separate and connected to the apparatus 10 via supply hoses and power lines. Plasma gas generally comprises an inert gas, including but not limited to He, Ne, Ar, $N_2$ or any combination thereof. Plasma gas is used to generate plasma and preferably to carry working gas into chamber 20 and between powered electrode 30 and grounded electrode 50.

In one embodiment a combination of a working gas and a plasma gas may be used. Alternatively, one or more different gases can be independently supplied to each of the flow channels 28 to create a patterned or varied treatment on surface 2. For example, apparatus 10 could provide a surface treatment of sections of surface with hydrophobic sections and a hydrophilic sections. A gas chosen for the desired treatment is chosen and provided to each flow channel 28 to treat that section of surface for the desired surface property. The flow rate of the plasma gas may range from about 100 sccm to about 10,000 sccm, preferably about 1000 sccm, and of the working gas may range from about 1 sccm to about 1000 sccm, preferably about 20 sccm.

Gas distribution device promotes the desired distribution of the gasses used in the process to flow channels 28 and ultimately to outlets 48. The distribution of gasses among the flow channels 28 may be equal or unequal, as desired. Gas distribution device includes one or more apertures 28 having powered electrodes 30 disposed therein. An arrangement having a powered electrode 30 dedicated to each aperture is illustrated, or, a plurality of powered electrodes 30 may be disposed in each aperture.

A flow channel 28 is provided between powered electrode 30 and grounded electrode 50. Single or plural powered and/or grounded electrodes 30, 50 may be disposed in a single flow channel 28. The flow channel 28 has a cross sectional area through which plasma gas and/or working gas may flow. The cross sectional area of the flow channel 28 does not include the powerable electrode 30 disposed therein. The cross sectional area of the flow channel 28 should be great enough to allow an adequate flow of the plasma gas and/or working gas therethrough.

The flow channel 28 is shaped such that it efficiently and adequately distributes excited species. The flow channel 28 provides a straight and unobstructed flow path for the flow of excited species from the area where interaction with the plasma occurs and more particularly from the specific point where interaction with the plasma ceases to occur. The flow path has a primary direction from this point to the target surface. The primary direction of the flow path is the principal flow direction from the point where interaction with the plasma ceases to the target surface. The flow path traverses this primary direction until the flow path intercepts the target surface.

The flow path may be straight and unobstructed throughout the primary direction and over the aforementioned distance. By straight it is meant there is a "see-through" area in the cross section of the flow channel 28 which does not require at least some of the excited species in the flow channel 28 to deviate in a curvilinear fashion to reach the target surface. By unobstructed it is meant that the excited species coincident the primary flow direction does not impinge upon another surface prior to intercepting the target surface.

As noted above, each flow channel 28 admits a plasma gas which forms a plasma upon interaction with the powered electrode 30/grounded electrode 50 pair. Likewise, a working gas may be admitted to the flow channel 28. The working gas generates excited species due to interaction with the plasma. The working gas should have adequate residence time with the plasma to allow generation of excited species from the working gas.

The gas(ses) exit(s) the flow channel 28 through an outlet 48. The outlet 48 of the flow channel 28 is juxtaposed with the target surface to allow the excited species to functionally interact with the target surface. Alternatively, working gas may be externally introduced. If so, the working gas should be externally introduced at a positon near the outlet 48 of the flow channel 28. This arrangement increases the liklihood that the plasma near the outlet 48 will operatively interact with the working gas to produce excited species.

If desired, a flow channel 28 may have plural outlets 48. However, this configuration is generally not desired, as it approaches the single plasma source/common header configuration Such a configuration is generally undesirable since the excited species dissipate and become inactive as the distance from the plasma source to the target surface increases. Alternatively, plural flow channels 28 may converge into a single outlet 48. However, this configuration is also generally not preferred as different working gasses and or different plasma gasses may be introduced into a single or common flow channel 28. This arrangement provides flexibility and zone control in the treatment of the workpiece. If plural flow channels 28 converge into a single outlet 48, the confluence of different working gasses and or plasma gasses will dilute the effect of using different gas combinations.

Powered electrodes 30 are electrically connectable to a power supply 100 that supplies the power to powered electrode 30. Power supply 100 may supply the power from an electrically connected power source that is either internal to apparatus 10 or external to apparatus 10. Power source may be a battery, having an optional DC/AC converter, or comprise an external AC source. If AC is used, either a continuous wave/plasma or pulsed wave plasma may be generated. With DC, typically the power source is modulated/pulsed at a suitable frequency. One power supply 100 may be connected to powered electrode 30. If desired, different power supplies 100 may be connected to multiple powered electrodes 30 to provide different voltages/amperages to different electrodes 30. The power levels may range from about 1 watt to about 40,000 watts (W), preferably from about 5 W to about 1000 W, more preferably from about 10 W to about 50 W. The voltage levels may range from about 150 V to about 40 kV, more preferably from about 400 V to about 20 kV.

The power supply 100 may use a radio frequency (RF) power source, optionally augmented with a microwave power source, if a microwave transparent channel is provided and the microwave radiation may reach the working gas and/or plasma gas. Typically the radio frequencies range from about 1 kHz to about 40 MHz, more preferably from about 10 kHz to about 30 kHz. Microwave frequencies range from about 1 GHz to about 20 GHz, preferably from about 1 GHz to about 3 GHz. Powered electrodes 30 may be disposed within apertures of grounded electrode 50, and are preferably coaxially disposed therein. This axi-symmetric arrangement of the powered electrode 30 and grounded electrode 50 promotes a stable, uniform plasma field. However, any arrangement is feasible if opposite electrodes 30, 50 are disposed on a common side of the workpiece as the workpiece is being treated. When powered electrodes 30 are placed within apertures, the arrangement forms a plurality of annular flow channels 28, between powered electrode 30 and grounded electrode 50. Each of these flow channels 28 has an outlet 48 through which the excited species may exit and impinge on the target surface.

The powerable electrodes 30 may have an elongate, substantially cylindrical-shape, optionally with a rounded tip. A shape which minimizes sharp corners on the powered electrode 30 is preferred, as the corners cause a higher intensity discharge to occur at such corners. This higher intensity discharge causes increased temperatures, creates less uniform plasma, and may lead to undesirable arcs ("hot spots").

Each powered electrode 30 may have a proximal end joined to bus bar 40 and a distal end opposite therefrom. Bus bar 40 is electrically connected to power supply 100. Powered electrodes 30 may be machined or formed from a single piece of conductive material to form powered electrodes 30 integral with the bus bar 40.

Powered electrodes 30 may be arranged in a circular array that circumscribes a central powered electrode 30. Powered electrodes 30 are preferably equally spaced from each other and equally sized. However, the powered electrodes 30 could be unequally distributed and spaced. Further, powered electrodes 30 could be unequal in size and/or have different power levels applied thereto.

For example, the array may comprise inner, intermediate and outer powerable electrodes 30 which define inner, intermediate and outer flow channels 28, respectively. The outer flow channels 28 may have a greater cross sectional area and/or be of greater density than the inner flow channels 28. By greater denisty it is meant the flow channels 28 are disposed on a closer pitch. This arrangement, or any other is suitable which allows a greater amount of excited species to impinge on the outer portions of the area of the surface being treated. By applying more excited species to the outer portion of the area being treated, the effects of ambient intrusion are advantageously offset.

The distal end of grounded electrode 50 need not be flat as shown. Instead, the grounded electrode 50 may have a generally convex shape, concave shape or any other shape that fits the workpiece desired to be treated. Distal end 34 of the powered electrode 30 may extend outward from or be recessed internal to the surface of the grounded electrode 50.

Electrodes 30, 50 of any embodiment described and claimed herein may have a variety of shapes and cross sections, and may be tapered, cylindrical, square, symmetrical, asymmetrical, grooved, perforate, imperforate, hollow, solid, straight, curved, etc. In an alternative to any of the embodiments described and claimed herein, the disposition of the grounded electrode 50 and powered electrode 30 may be transposed. For example, in this alternative embodiment of FIGS. 1–3, the groundable electrodes 50 comprise a plurality of elongate probes disposed within a powerable electrode 30 comprising a conductive block having a plurality of apertures receptive to the groundable electrodes 50.

Powered electrode 30 may be made as follows. A conductive material, typically metal having a melting point less than 300 degrees C. is melted and poured into a preformed hollow tube made of glass or other dielectric 60 material having a blind aperture which accepts the conductive material. Metal such as tin plus 2% silver solder has been found to work well for the conductive material.

An electrical lead wire 39 is disposed in the conductive material before solidifies. The lead wire may be disposed in the dielectric 60 tube before or after adding the liquid conductive material thereto. When frozen, the metal within the dielectric 60 tube 60 forms a probe-like powerable or groundable electrode 50 30 or 50 encased by the dielectric 60 tube. Each suchelectrode 30 may have one or more lead wires 39 protruding from the its proximal end 38. Such lead wire 39 connects the electrode 30, 50 to power or ground, as desired.

Figure 4:
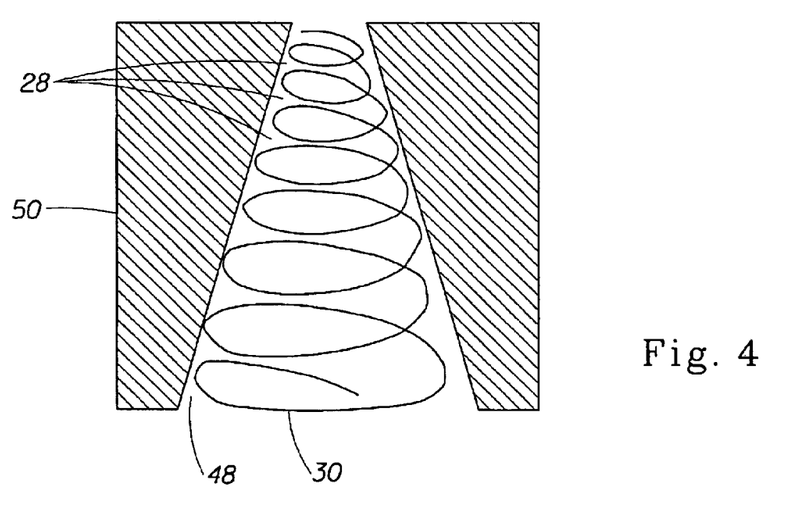
FIG. 4 is a perspective view of a helical electrode disposed in a flow channel.
Figure 5:
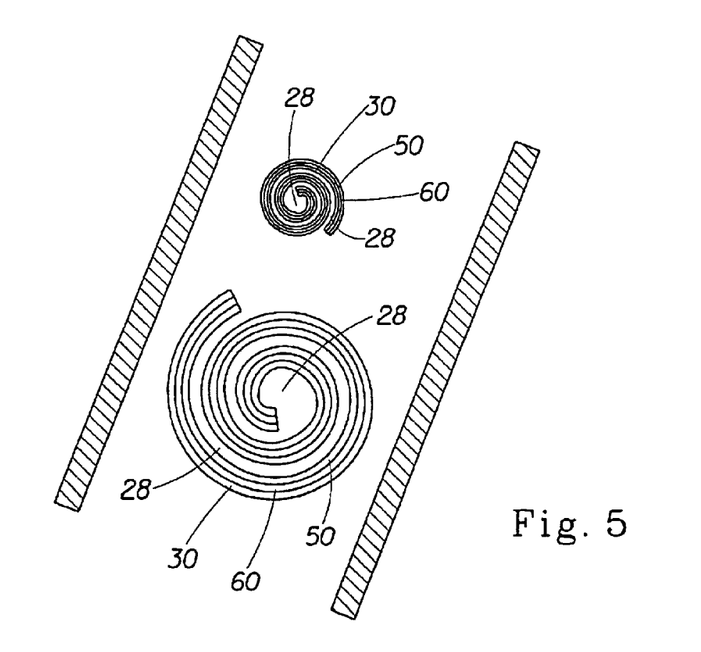
FIG. 5 is a perspective view of plural spiral electrodes disposed in a flow channel.

Referring to FIGS. 4–5, the apparatus 10 may comprise spiral powered electrodes 30, 50. Spiral powered electrodes 30, as used herein, include electrodes having a planar configuration, such as volutes/involutes, and three-dimensional configurations, such as a helix, and include both clockwise and counterclockwise windings, symmetric and asymmetric, concencetric and eccentric geometries of circles ovals, regular or irregular polygons, etc. having equally spaced and/or unequally spaced coils.

A single spiral powered electrode 30 may be disposed in a flow channel 28 defined by a grounded electrode 50. If the grounded electrode 50 is of constant radius, as for example occurs in a cylindrically shaped aperture type of grounded electrode 50, as described above, the spacing between each coil of the spiral and the electrode is different. In a preferred embodiment, the grounded electrode 50 may also be spiral shaped, to provide more uniform spacing between opposite electrodes 30, 50.

Alternatively in a more preferred embodiment the powered electrode 30 and grounded electrode 50 may be formed from a laminate comprising two opposite electrodes 30, 50 separated by a dielectric 60. Either the powered electrode 30 or grounded electrode 50 may be internal or external to the laminated spiral coils. It is only necessary that the powered electrode 30 and grounded electrode 50 be spaced apart a distance sufficient to allow the generation of plasma therebetween. Optionally, a space may be interposed between the dielectric 60 and grounded electrode 50.

If a powered electrode 30 is disposed in a flow channel 28 defined by a grounded electrode 50, each coil of the powered electrode 30 forms an electrode pair with the grounded electrode 50. Likewise, if the laminated spiral having a coiled powered electrode 30 separated from the grounded electrode 50 by a dielectric 60 is selected, each coil may be thought of as an electrode pair. In either configuration each space between adjacent coils of the spiral effectively comprises a flow channel 28. Thus, a single spiral powered electrode 30 provides plural flow channels 28 within the meaning of the invention.

If desired, plural spiral powered electrodes 30 may be disposed in a common flow channel 28. The plural powered electrodes 30 may be planar and disposed in a common plane, spaced radially and circumferentially apart or may be planar. Alternatively, the plura spiral electrodes may be axially spaced apart in separate parallel or skewed planes. Alternatively, plural congruent, and optionally concentric, helical powered electrodes 30 may be utilized. If the plural helical powered electrodes 30 are utilized with a grounded electrode 50 defining the flow channel 28, preferably the flow channel 28 is tapered to maintain constant spacing between the electrode pairs 30, 50.

Figure 6:
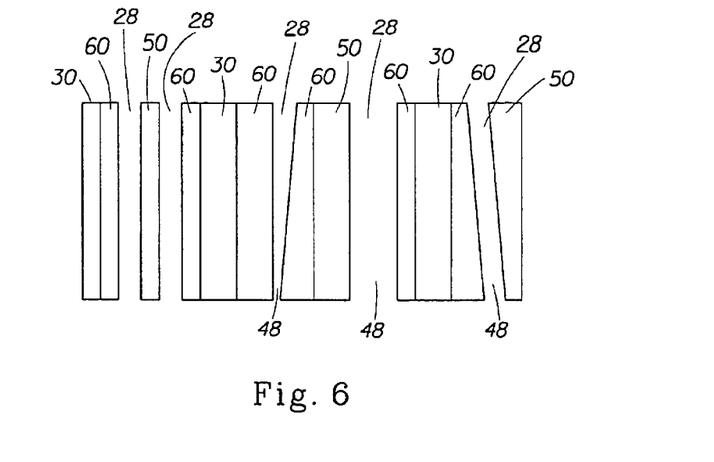
FIG. 6 is a side elevational view of an electrode assembly comprising parallel plates defining flow channels.

Referring to FIG. 6, if desired, the electrodes 30, 50 may be comprised of a repeating pattern of electrically conductive plates, dielectrics 60 and flow channels 28 therebetween. The plates and flow channels 28 may be skewed or parallel, of equal or unequal thickness and/or dimensions within the plane of the plate, may be comprised of the same materials, different materials, or combinations of materials, have equal or unequal power levels applied to the powered electrodes 30, etc.

The electrodes 30, 50 and dielectric 60 are arranged in a repeating pattern as shown, and may have as many repeating units as desired. The grounded electrodes 50 may or may not be insulated from the flow channel 28 by an optional dielectric 60. The pattern comprises a powered electrode 30, dielectric 60, flow channel 28, optional dielectric 60, grounded electrode 50, optional dielectric 60, flow channel 28, dielectric 60, powered electrode 30, dielectric 60, etc. and repeats as often as necessary to yield the desired number of flow channels 28.

The plasma gas and working gas flow through the flow channel 28 between the two dielectrics 60 or between the dielectric 60 and grounded electrode 50. The plasma gas is excited by the powered electrode 30 into plasma and generates excited species in the working gas. The excited species pass through the flow channel 28 and onto the target surface.

Figure 7:
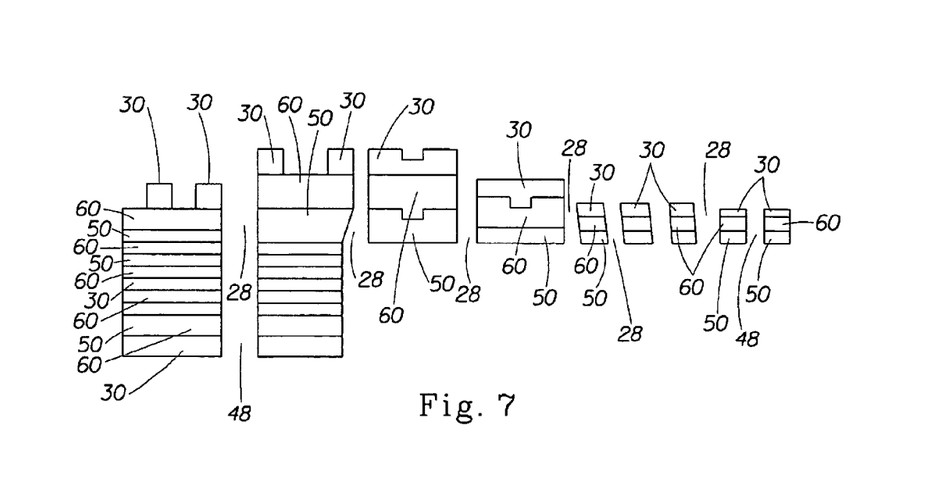
FIG. 7 is a side elevational view of a laminate electrode assembly having flow channels therethrough.

Referring to FIG. 7, the electrodes 30, 50, may comprise a gas permeable laminate of plates. The laminate may comprise in as many repeating units as desired. Each laminate comprises laminae in a repeating pattern of a powered electrode 30, dielectric 60, grounded electrode 50, powered electrode 30, etc. The laminae may be of equal or unequal thickness, constant or variable thicknesses, may or may not be coextensive, curvilinear in one or more planes or flat, etc. as desired. The powered electrodes 30 may have equal or unequal power levels applied thereto.

In a preferred embodiment the laminate may comprise plural powered electrodes 30 smaller than the grounded electrode 50 and/or dielectric 60 and disposed on a common dielectric 60. Each powered electrode 30 may have a width of two mm or less. This arrangement provides the benefit that different power levels may be applied to different powerable electrodes 30. For any of the embodiments described and claimed herein, applying different power levels, as a function of time or the position of the electrodes 30 allows the electrode 30 to be tailored to the specific plasma gas in a particular flow channel 28. Tailoring the power of the electrode 30 to a particular gas allows gasses with different breakdown voltages to be advantageously used. Using different gasses in different flow channels 28 allows for patterning the surface modification effect at different positions in the workpiece.

The laminate may be perforate. If so, each perforation comprises a flow channel 28 and may may have a dimension of 10 micrometers to 20 millimeters and preferably 10 to 200 micrometers. The flow channels 28 may be of regular or irregular size, shape and spacing. The working gas and plasma gas flow through the flow channels 28 to produce the plasma and excited species, as described above.

EXAMPLE 1

The embodiment of FIGS. 1–3 was used to deposit a monomeric coating on a piece of 100% cotton fabric. Powered electrodes 30 consisted of glass tubes having an inside diameter of of about 1.8–2.0 mm, and were filled with Tin and 2% silver solder. The glass wall provided a dielectric thickness of about 0.6 mm. A thin metal wire 39 was incorporated into the solder before it solidified and were used to connect the electrodes 30 to the power supply 100.

Each powered electrode 30 was centered in an aperture having a diameter of about 4 millimeters in the grounded electrode block 50 to thereby form an array of nine powered electrodes. The array comprised eight equally spaced powered electrodes 30 on a 49 millimeter diameter circle having a single central powered electrode 30. Each powered electrode 30 had a length in the axial direction of about 65 millimeters.

A mixture of Helium plasma gas and PFMCH working gas was passed through each of the flow channels 28 The cotton fabric was spaced from the powered electrode 30 assembly, in ambient air a distance of about 5 mm. Approximately 3.5 kV RMS of voltage at about 15 kHz was applied to the electrode array. The gas flow rates, were measured and calculatedat Helium plasma gas of 1000 sccm and PFMCH working gas 26 sccm. The reatment time was 9 minutes and covered a fabric area having a diameter of about 6 cm.

Following treatment, water droplets, normally instantly absorbed by this cotton fabric were found to bead up and roll off the fabric, indicating the surface was now hydrophobic.

The fabric was analyzed for Fluorine (F), using standard elemental analysis techniques. The results are given in Table 1.

TABLE 1

| Sample Description | Fluorine Content (%) | Fluorine Content (ppm) |
|---|---|---|
| Untreated, control | 0.003 | 30 |
| Treated | 0.942 | 9420 |

EXAMPLE 2

The apparatus 10 of Example 1 was used with different working gasses and treatment times to determine their effects on the cotton fabric. Following treatment, xray photonelectron spectroscopy (XPS) analyses of the treated fabric samples were performed. The experimental conditions and the XPS results are given in Table 2 A greater percentage of Fluorine in the sample, compared to the percentages of Oxygen and Carbon indicates greater coverage of the surface of the fabric fibers with a flourocarbon plasma polymer coating. The untreated fabric has predominantly Oxygen and Carbon at the surface with negligible Fluorine content. The percentage of Fluorinein the sample also correlates well with the degree of hydrophobicity of the fabric visually observed by putting drops of water on the fabric surface. At greater Fluorine percentages on the samples, more the water was noted to bead up on the surfaceAt 70% Fluorine the water drops were found to roll off the fabric surface without being absorbed.

TABLE 2

| Expt# | Working Gas | Carrier Flow Rate SCCM | Voltage, RMS(kV) | Treatmnt Time (min) | Monomer Used (ml) | Mass % F | Mass % O | Mass % C |
|---|---|---|---|---|---|---|---|---|
| 1 | He | 3000 | 0.6 | 10 | 6.5 | 3.08 | 48.08 | 48.85 |
| 2 | He | 1000 | 3.6 | 13 | 3.0 | 70.88 | 14.30 | 14.82 |
| 3 | He | 500 | 2.0 | 15 | 3.5 | 6.04 | 47.44 | 46.52 |
| 4 | Ar + He | 300 500 | 1.5 | 15 | 7.0 | 29.60 | 35.15 | 35.25 |
| 5 | He | 1000 | 4.0 | 9 | 1.0 | 76.90 | 9.42 | 13.69 |

EXAMPLE 3

Table 3 shows the fluorine content on the cotton fabric for a variety of treatment times. Again, the apparatus 10 of Examples 1–2 was used with a perfluoromethylcyclohexane working gas at a flow rate of about 30 sccm and a Helium plasma gas at a flow rate of 1000 sccm. Process parameters were: 15 kHz frequency and approx 4 kV RMS (12 kV peak-to-peak). Experiment 6 used a cellulosic filter paper for the sample. All showed hydrophobic modification of the cotton surface, using water droplet test. The presence of significant quantities of $CF_2$, in Experiments 1–4, indicates a plasma polymer coating of PFMCH monomer was present on the surface of the fabric. This plasma polymer coatings is covalently bonded to the surface. The coating did not wash off by hand and provided the desired durable bydrophobic surface modification.

TABLE 3

| Expt# | Treatment Time (min) | Monomer Used (ml) | Relative % CF2 (surface) XPS analysis of | Relative % CF3 (surface) analysis of | Mass % F (surface) Surface | Mass % F (bulk) Elemental analysis of bulk |
|---|---|---|---|---|---|---|
| 1 | 3 | 1 | 31.1 | 7.7 | 53.3 | 0.843 |
| 2 | 6 | 2 | 30.6 | 7.2 | 57.9 | 1.23 |
| 3 | 9 | 2.5 | 21.0 | 4.3 | 71.1 | 2.27 |
| 4 | 12 | 3 | 16.0 | 5.0 | 71.6 | 2.01 |
| 5 | Untreated (control) | | 0 | 0 | 3.9 | .0069 |
| 6 | 10 (vacuum) | 1 | 32.7 | 20.8 | 85.5 | |

What is claimed is:

1. An atmospheric-pressure, plasma generating apparatus for treating a surface of a workpiece, said apparatus comprising:
   a plurality of powerable electrodes connectable to one or more power supplies and powerable thereby;
   at least one groundable electrode connectable to a ground,
   a plurality of dielectrics, wherein a dielectric of said plurality is associated with each said powerable electrode, each said dielectric being intermediate said powerable electrode and said at least one groundable electrode wherein each said dielectric contacts said powerable electrode;
   a first plurality of said powerable electrodes and said at least one groundable electrode being disposed in pairs, each of said pairs generating a plasma zone and operatively associated with a second plurality of flow channels, wherein said plurality of electrodes disposed in said flow channels comprises elongated electrodes disposed in elongate flow channels, whereby a plasma gas can flow through said flow channels and thereby produce a plasma therein upon interaction with said powerable electrode when powered, said plasma being capable of interacting with a working gas to thereby produce excited species, and
   a third plurality of outlets from said flow channels, said outlets being juxtaposable with a workpiece whereby the excited species may flow from interaction with said plasma through said outlets to impinge on the surface of the workpiece, said flow of said excited species being in a primary direction which is straight and unobstructed from said plasma to said surface of said workpiece.

2. An apparatus according to claim 1 wherein said plurality of electrodes disposed in said flow channels are powerable, each said powerable electrode extending from a proximal end to a distal end, said distal end being juxtaposed with said outlet of said flow channel, said cross sectional area of said powerable electrode not increasing as said distal end is approached.

3. An apparatus according to claim 2 wherein said flow channels are disposed in an array comprising inner flow channels and outer flow channels, said outer flow channels having a greater cross-sectional area and/or density than said inner flow channels.

4. A apparatus according to claim 1, her in at least one said powerable electrode of said plurality of powerable electrodes is spaced about 10 micrometers to about 20 mm from at least one said groundable electrode.

5. An apparatus according to claim 1 comprising at least one electrode having a spiral configuration, said spirally configured electrode substantially circumscribing or being substantially circumscribed by an opposite electrode to define a flow channel therebetween.

6. An apparatus according to claim 5 wherein said spirally configured electrode has a helical configuration.

7. An apparatus according to claim 5 comprising plural spirally configured electrodes disposed in a common flow channel.

8. An apparatus according to 1 further comprising a gas source, said gas source being in communication with one or more of said flow channels, whereby said gas source can provide gas to said flow channels to cause gas flow therethrough, and provide an unequal gas distribution through different said flow channels.

9. An apparatus according to claim 8 wherein said gas source provides different plasma gases and/or different working gases to said flow channels.

10. An apparatus according to claim 9 where in said different working gases and/or said different plasma gases are convergingly provided to a common flow channel.

11. An apparatus according to claim 1 comprising a plurality of powerable electrodes, said powerable electrodes being mutually different in size.

12. An apparatus according to claim 1 further comprising one or more power sources, wherein different said powerable electrodes have different power levels applied thereto.

13. An apparatus according to claim 1 wherein said dielectric comprises glass.

* * * * *

UNITED STATES PATENT AND TRADEMARK OFFICE
CERTIFICATE OF CORRECTION

PATENT NO. : 6,821,379 B2
DATED : November 23, 2004
INVENTOR(S) : Datta et al.

It is certified that error appears in the above-identified patent and that said Letters Patent is hereby corrected as shown below:

Column 13,
Line 36, delete "elongated" and insert -- elongate --.

Column 14,
Line 22, delete "A apparatus according to claim 1, her in" and insert therefor
-- An apparatus according to claim 1, wherein --.
Line 45, please delete "where in" and insert therefor -- wherein --.

Signed and Sealed this

Seventh Day of June, 2005

JON W. DUDAS
*Director of the United States Patent and Trademark Office*